US006506714B1

(12) United States Patent
Soriano et al.

(10) Patent No.: US 6,506,714 B1
(45) Date of Patent: Jan. 14, 2003

(54) METHOD FOR STOPPING HYSTERESIS

(75) Inventors: Zenaida Soriano, Muntinlupa (PH); Ma. Theresa Lumain, Quezon (PH)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 09/702,491

(22) Filed: Oct. 31, 2000

(51) Int. Cl.$^{7}$ .................................................. A61K 7/00

(52) U.S. Cl. ....................... 510/130; 510/159; 510/481; 510/488

(58) Field of Search ................................ 510/130, 159, 510/488, 481

(56) References Cited

U.S. PATENT DOCUMENTS

| | | | | | |
|---|---|---|---|---|---|
| 2,089,305 | A | | 8/1937 | Stickdorn | 87/5 |
| 2,097,737 | A | | 11/1937 | Pickett et al. | 87/5 |
| 2,912,385 | A | | 11/1959 | Golub et al. | 252/132 |
| 3,361,213 | A | | 1/1968 | Savins | 169/1 |
| 3,723,328 | A | | 3/1973 | Pelizza | 252/111 |
| 4,310,433 | A | | 1/1982 | Stiros | 252/132 |
| 5,208,074 | A | | 5/1993 | Kosal | 427/389 |
| 5,308,526 | A | * | 5/1994 | Dias et al. | 252/125 |
| 5,549,758 | A | * | 8/1996 | Murch et al. | 134/6 |
| 5,902,779 | A | | 5/1999 | Cormier | 510/159 |
| 5,977,039 | A | * | 11/1999 | Gordon et al. | 510/130 |

FOREIGN PATENT DOCUMENTS

| | | | |
|---|---|---|---|
| EP | 0011166 | 10/1979 | C11D/10/04 |
| GB | 1572606 | 4/1976 | C11D/10/06 |
| GB | 2232420 | 12/1990 | C11D/10/00 |

* cited by examiner

*Primary Examiner*—Necholus Ogden
(74) *Attorney, Agent, or Firm*—Martin B. Barancik

(57) ABSTRACT

An aqueous, clear, cleansing composition comprising (a) a cleansing effective amount of a potassium salt of a long chain alkyl carboxylic acid or mixture thereof, the pH of said composition being from about 10.0 to about 11.0.

2 Claims, No Drawings

METHOD FOR STOPPING HYSTERESIS

BACKGROUND OF THE INVENTION

Cleansing the skin is a desired result throughout the world. However the skin feel achieved during and after the process is subject to many different factors including cultural variations. In North America and Europe, it is generally desired to have a slippery feel. However many people in Asia prefer to have a feel which is less slippery and approaching or achieving a "squeaky clean" feeling. Another desired characteristic is a transparent composition, that is, one that a person can see images through. One of the factors important in achieving clarity is a low cloud point, the temperature at which a clear composition begins to become hazy. Having a low cloud point is of significance in countries where the climate is temperate and particularly where it is subtropical or tropical. Generally a cloud point of about 4–6° C. or even lower is desirable.

This is particularly significant where the aqueous composition undergoes hysteresis when it goes through its cloud point. Generally, when a composition descends through its cloud point it begins to become hazy. However, when the temperature is raised past its cloud point it becomes clear once again in a short period of time, for example usually no more than about 2 or 3 minutes at a temperature 1 or 2° C. about its cloud point. However certain compositions do not undergo this rapid change to clarity. Rather it takes a relatively lengthy period of time, even at a temperature significantly above its cloud point to achieve clarity once again. This physical phenomenon is oftentimes referred to as hysteresis.

This phenomenon has recently been encountered in a clear aqueous soap solution wherein the surfactants are primarily potassium salts of long chain carboxylic acids. After significant experimentation including a number of erroneous attempts to solve the problem, it has been discovered that the cloud point of such compositions can be significantly lowered as well as the removal of the significant issue of hysteresis through raising the pH of the composition. Surprisingly the high pH does not make the composition irritating as measured by clinical testing.

SUMMARY OF THE INVENTION

In accordance with the invention, there is an aqueous, clear cleansing composition comprising a cleansing effective amount of a potassium salt of a long chain alkyl carboxylic acid or mixtures thereof, the pH of said composition being from about 10.0 to about 11.0.

A further aspect of the invention is a method for lowering the cloud point of an aqueous clear cleansing composition having a cleansing amount of a potassium salt of a long chain alkyl carboxylic acid or a mixture thereof which comprises adjusting the pH of the composition to about 10.0 to about 11.0. A further benefit of the higher pH is that no hysteresis occurs even with the lower cloud point.

A pH of no more than about 10.8 can also be employed.

DESCRIPTION OF THE PREFERRED EMBODIMENTS

The long chain alkyl carboxylate potassium salt or mixture thereof can have from about eight to about twenty carbon atoms, desirably about ten to about eighteen carbon atoms. Generally in order to cleanse the skin, there should be at least about 1 wt. % of the composition of the long chain alkyl carboxylate potassium salt or mixture thereof, desirably 2, 3, 4 or 5 wt. % of the composition. The maximum amount varies as the desired thickness of the composition or irritational aspects, but generally no more than about 30 wt. %, desirably 25 wt. % of the composition should be the potassium salt or mixture thereof.

Other anionic surfactants can be present in the composition such as amphoteric, nonionic, and cationic surfactants, although the composition can be without any of these surfactant families, particularly the cationic.

Examples of these surfactants include anionic nonsoap surfactants such as can be exemplified by the alkali metal salts of organic sulfate having in their molecular structure an alkyl radical containing from about 8 to about 22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols ($C_8$–$C_{18}$ carbon atoms), sodium coconut oil fatty acid monoglyceride sulfates and sulfonates as well as alpha olefin sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine; and others known in the art for example taurates, phosphate, and those listed in the *McCutcheon's Encyclopedia of Surfactants.*

Although not necessary other surfactants may be present in the composition. Examples of these surfactants include zwitterionic surfactants can be exemplified by those which can be broadly described as derivatives of aliphatic quaternary ammonium, phosphonium, and sulfonium compounds, in which the aliphatic radicals can be straight chain or branched and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

$$\begin{matrix} (R)^3_x \\ | \\ R^2Y^{(+)}\text{—}CH_2\text{—}R^4\text{—}Z^{(-)} \end{matrix}$$

wherein $R^2$ contains an alkyl, alkenyl, or hydroxy alkyl radical of from about 8 to about 18 carbon atoms, from 0 to about 10 ethylene oxide moieties and from 0 to 10 glyceryl moiety; Y is selected from the group consisting of nitrogen, phosphorus, and sulfur atoms; $R^3$ is an alkyl or monohydroxyalkyl group containing 1 to about 3 carbon atoms; x is 1 when Y is a sulfur atom and 2 when Y is a nitrogen or phosphorus atom, $R^4$ is an alkylene or hydroxyalkylene of from 0 to about 4 carbon atoms and Z is a radical selected from the group consisting of carboxylate, sulfonate, sulfate, phosphonate, and phosphate groups.

Examples include:

4-[N,N-di(2-hydroxyethyl)-N-octadecylammonio]-butane-1-carboxylate;

5-[S-3-hydroxypropyl-S-hexadecylsulfonio]-3 hydroxypentane-1-sulfate

3-[P,P,P-diethyl-P 3,6,9 trioxatetradecyl-phosphonio]-2-hydroxypropane-1-phosphate 3-[N,N-dipropyl-N-3 dodecoxy-2-hydroxy-propylammonio]-propane-1-phosphonate 3-(N,N-di-methyl-N-hexadecyl-ammonio) propane-1-sulfonate; 3-(N,N-dimethyl-N-hexadecylammonio)-2-hydroxypropane-1-sulfonate 4-(N,N-di(2-hydroxyethyl)-N-(2 hydroxydodecyl) ammonio]-butane-1-carboxylate 3-[S-ethyl-S-(3-dodecoxy-2-hydroxy-propyl)sulfonio]-propane-1-phosphate 3-(P,P-dimethyl-P-dodecylphosphonio)-propane-1-phosphonate; and 5-[N,N-di(3-hydroxypropyl)-N-hexadecyl-ammonio]-2-hydroxy-pentane-1-sulfate.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, N-alkyltaurines, such as the one prepared by reacting dodecylamine with sodium isethionate according to the teaching of U.S. Pat. No. 2,658,072, N-higher alkyl aspartic acids, such as those produced according to the teaching of U.S. Pat. No. 2,438,091, and the products sold under the trade name "Miranol" and described in U.S. Pat. No. 2,528,378. Other amphoterics such as betaines are also useful in the present composition.

Examples of betaines useful herein include the high alkyl betaines such as cocodimethyl carboxymethyl betaine, lauryl dimethyl carboxymethyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl) carboxymethyl betaine, oleyl dimethyl gamma-carboxypropyl betaine, lauryl bis-(2-hydroxypropyl) alpha-carboxyethyl betaine, etc. The sulfobetaines may be represented by cocodimethyl sulfopropyl betaine, stearyl dimethyl sulfopropyl betaine, amido betaines, amidosulfobetaines, and the like.

Many cationic surfactants are known to the art. By way of example, the following may be mentioned:

stearyldimethylbenzyl ammonium chloride;

dodecyltrimethylammonium chloride;

nonylbenzylethyldimethyl ammonium nitrate;

tetradecylpyridinium bromide;

laurylpyridinium chloride;

cetylpyridinium chloride laurylpyridinium chloride;

laurylisoquinolium bromide;

ditallow(hydrogenated)dimethyl ammonium chloride;

dilauryldimethyl ammonium chloride; and stearalkonium chloride.

Additional cationic surfactants are disclosed in U.S. Pat. No. 4,303,543. See column 4, lines 58 and column 5, lines 1–42, incorporated herein by references. Also see *CTFA Cosmetic Ingredient Dictionary*, 4th Edition 1991, pages 509–514 for various long chain alkyl cationic surfactants; incorporated herein by references.

Nonionic surfactants can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.
2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.
3. The condensation product of aliphatic alcohols having from 8 to 18 carbon atoms, in either straight chain or branched chain configuration with ethylene oxide, e.g., a coconut alcohol ethylene oxide condensate having from 10 to 30 moles of ethylene oxide per mole of coconut alcohol, the coconut alcohol fraction having from 10 to 14 carbon atoms. Other ethylene oxide condensation products are ethoxylated fatty acid esters of polyhydric alcohols (e.g., Tween 20-polyoxyethylene (20) sorbitan monolaurate).
4. Long chain tertiary amine oxides corresponding to the following general formula:

$$R_1R_2R_3N\rightarrow O$$

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and, $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyl-di(2-hydroxyethyl) amine oxide, dimethyloctylamine oxide, dimethyldecylamine oxide, dimethyltetradecylamine oxide, 3,6,9 trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formula:

$$RR'R''P\rightarrow O$$

wherein R contains an alkyl, alkenyl or monohydroxyalkyl radical ranging from 8 to 20 carbon atoms in chain length, from 0 to about 10 ethylene oxide moieties and from 0 to 1 glyceryl moiety and R' and R" are each alkyl or monohydroxyalkyl groups containing from 1 to 3 carbon atoms. The arrow in the formula is a conventional representation of a semipolar bond.

Examples of suitable phosphine oxides are:

dodecyldimethylphosphine oxide, tetradecylmethylethyl phosphine oxide, 3,6,9-trioxaoctadecyldimethyl-phosphine oxide, cetyldimethylphosphine oxide, 3-dodecoxy-2-hydroxypropyldi(2-hydroxyethyl) phosphine oxide stearyldimethyl-phosphine oxide, cetylethyl propylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxy-ethyl)phosphine oxide, tetradecyl-methyl-2-droxypropylphosphine oxide, oleyldimethylphosphine oxide, and 2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3 methoxytridecylmethyl sulfoxide, 3-hydroxytridecyl methyl sulfoxide, 3-hydroxy-4-dodecoxybutyl methyl sulfoxide.

7. Alkylated polyglycosides include wherein the alkyl group is from about 8 to 20 carbon atoms, preferably about 10 to about 18 carbon atoms and the degree of polymerization of the glycoside is from about 1 to about 3, preferably about 1.3 to about 2.0.

The additional surfactants can be present in the compositions from about 0.5 to about 15 wt. % of the composition, desirably from about 0.75 to about 12 wt. % of the composition.

Water is present in the composition at quantities of at least about 50 wt. % of the composition, desirably at least about 60, 70 or 80 wt. % of the composition.

Additionally other components can be present in the composition including antimicrobial compositions such as Triclosan, perfumes, chelants such as EDTA, preservatives, vegetable extracts, colorants, thickeners, and the like.

The term "clarity" as used in the specification and claims means the product is visually clear. When the product is lowered below its cloud point temperature which can be 0° C. or even lower, such as −2, −3 or even −5° C., the composition becomes hazy. However, when the temperature is raised above its cloud point and held for a short period of time, nor more than about two (2) minutes, but can be one (1) minute or less, the composition once more becomes visually clear. PH is measured by an electronic Beckman pH meter at 25° C.

The hysteresis of the noncloud point stabilized system is visually noted at least by a minimum of haze in the composition. Below is a comparative example and an example of the invention showing the benefits and advantages of the inventive composition.

COMPARISON EXAMPLE 1

A clear aqueous composition has the following components

| Component | Weight % |
|---|---|
| Potassium soap | 18.0 |
| Cocamide DEA | 2.70 |
| Lauryl polyglucose | 2.50 |
| Perfume | 1.0 |
| Sorbitol | 0.64 |
| Hydroxyethylcellulose | 0.60 |
| Potassium hydroxide | 0.142 |
| Sunflower/acacia extract | 0.10 |
| Preservative, UV protestant, colorant | 0.43 |
| Balance - water | QS |
| Total Materials | 100.00 |

This composition has a pH of 9.6 and a cloud point of 4–6° C. The temperature of the composition is lowered to 3° C. Haze appears. The temperature of the composition is raised to 17° C. and held there for about 18 hours. The haze remains.

EXAMPLE 1

The same composition is prepared as in comparative Example 1 however its pH is adjusted to 10.5. Its cloud point is now about 0° C. The temperature is lowered to about −2° C. The composition develops a haze. The temperature is now raised to about 2° C. and held there for about 2 minutes. The composition is clear according to the aforestated visual clarity test. No hysteresis occurs. Additionally, the composition is non-irritating and passes the stability and preservative effectiveness test.

What is claimed is:

1. A method for stopping hysteresis from occurring at pH 9.6 in a clear aqueous composition comprising about 4 to about 25 wt. % of a potassium salt of a long chain alkyl carboxylic acid or a mixture thereof which comprises adjusting the said composition pH to about 10.0 to about 10.8 and raising the composition temperature from 2° C. below the cloud point to 2° C. above the cloud point and having haziness disappear in a maximum of about 2 minutes at the temperature 2° C. above the cloud point.

2. A method in accordance with claim 1 wherein a nonionic surfactant or mixture thereof is also present in the composition.

* * * * *